US011935158B2

(12) United States Patent
Christodoulou et al.

(10) Patent No.: US 11,935,158 B2
(45) Date of Patent: Mar. 19, 2024

(54) SYSTEMS AND METHODS OF ON-THE-FLY GENERATION OF 3D DYNAMIC IMAGES USING A PRE-LEARNED SPATIAL SUBSPACE

(71) Applicant: Cedars-Sinai Medical Center, Los Angeles, CA (US)

(72) Inventors: Anthony Christodoulou, Los Angeles, CA (US); Zhaoyang Fan, Palos Verdes Estates, CA (US); Debiao Li, South Pasadina, CA (US); Pei Han, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 17/997,639

(22) PCT Filed: May 4, 2021

(86) PCT No.: PCT/US2021/030667
§ 371 (c)(1),
(2) Date: Oct. 31, 2022

(87) PCT Pub. No.: WO2021/226095
PCT Pub. Date: Nov. 11, 2021

(65) Prior Publication Data
US 2023/0222708 A1 Jul. 13, 2023

Related U.S. Application Data

(60) Provisional application No. 63/019,791, filed on May 4, 2020.

(51) Int. Cl.
*G01V 3/00* (2006.01)
*G01R 33/48* (2006.01)
*G06T 11/00* (2006.01)

(52) U.S. Cl.
CPC ........ *G06T 11/005* (2013.01); *G01R 33/4818* (2013.01); *G06T 11/006* (2013.01); *G06T 2211/428* (2013.01)

(58) Field of Classification Search
CPC .............. G01R 33/3415; G01R 33/543; G01R 33/5659; G01R 33/36; A61B 5/055
(Continued)

(56) References Cited

U.S. PATENT DOCUMENTS

| 2008/0183067 A1* | 7/2008 | Shu ..................... G01R 33/4824 600/410 |
| 2014/0044335 A1* | 2/2014 | Johnson ................ G06T 11/003 382/131 |

(Continued)

OTHER PUBLICATIONS

International Search Report and Written Opinion dated Aug. 3, 2021 in PCT/US2021/030667.

(Continued)

*Primary Examiner* — Walter L Lindsay, Jr.
*Assistant Examiner* — Frederick Wenderoth
(74) *Attorney, Agent, or Firm* — Nixon Peabody LLP (57) ABSTRACT

A method for performing real-time magnetic resonance (MR) imaging on a subject is disclosed. A prep pulse sequence is applied to the subject to obtain a high-quality special subspace, and a direct linear mapping from k-space training data to subspace coordinates. A live pulse sequence is then applied to the subject. During the live pulse sequence, real-time images are constructed using a fast matrix multiplication procedure on a single instance of the k-space training readout (e.g., a single k-space line or trajectory), which can be acquired at a high temporal rate.

22 Claims, 10 Drawing Sheets

(58) Field of Classification Search
USPC .......................................................... 324/309
See application file for complete search history.

(56) References Cited

U.S. PATENT DOCUMENTS

| | | | |
|---|---|---|---|
| 2017/0069115 | A1 | 3/2017 | Saito |
| 2017/0325709 | A1* | 11/2017 | Nayak ............... G01R 33/5601 |
| 2018/0306882 | A1 | 10/2018 | Li |
| 2020/0033434 | A1 | 6/2020 | Stern |

OTHER PUBLICATIONS

De Los Santos J, Popple R, Agazaryan N, Bayouth JE, Bissonnette JP, Bucci MK, et al. Image guided radiation therapy (IGRT) technologies for radiation therapy localization and delivery. Int J Radiat Oncol Biol Phys. 2013;87(1):33-45.

Dawson LA, Jaffray DA. Advances in image-guided radiation therapy. J Clin Oncol. 2007;25(8):938-46.

Otazo R, Lambin P, Pignol JP, Ladd ME, Schlemmer HP, Baumann M, Hricak H. MRI-guided Radiation Therapy: An Emerging Paradigm in Adaptive Radiation Oncology. Radiology. Dec. 22, 2020:202747.

Raaymakers BW, Lagendijk JJ, Overweg J, Kok JG, Raaijmakers AJ, Kerkhof EM, et al. Integrating a 1.5 T MRI scanner with a 6 MV accelerator: proof of concept. Phys Med Biol. 2009;54(12):N229-37.

Raaymakers BW, Jurgenliemk-Schulz IM, Bol GH, Glitzner M, Kotte A, van Asselen B, et al. First patients treated with a 1.5 T MRI-Linac: clinical proof of concept of a high-precision, high-field MRI guided radiotherapy treatment. Phys Med Biol. 2017;62(23):L41-L50.

Mutic S, Dempsey JF. The ViewRay system: magnetic resonance-guided and controlled radiotherapy. Semin Radiat Oncol. 2014;24(3):196-9.

Huttinga NRF, van den Berg CAT, Luijten PR, Sbrizzi A. MR-MOTUS: model-based non-rigid motion estimation for MR-guided radiotherapy using a reference image and minimal k-space data. Phys Med Biol. 2020;65(1):015004.

Stemkens B, Tijssen RH, de Senneville BD, Lagendijk JJ, van den Berg CA. Image-driven, model-based 3D abdominal motion estimation for MR-guided radiotherapy. Phys Med Biol. 2016;61(14):5335-55.

Dietz B, Yip E, Yun J, Fallone BG, Wachowicz K. Real-time dynamic MR image reconstruction using compressed sensing and principal component analysis (CS-PCA): Demonstration in lung tumor tracking. Med Phys. 2017;44(8):3978-89.

Dietz B, Yun J, Yip E, Gabos Z, Fallone BG, Wachowicz K. Single patient convolutional neural networks for real-time MR reconstruction: a proof of concept application in lung tumor segmentation for adaptive radiotherapy. Phys Med Biol. 2019;64(19):195002.

Feng L, Tyagi N, Otazo R. MRSIGMA: Magnetic Resonance SIGnature MAtching for real-time volumetric imaging. Magn Reson Med. 2020;84(3):1280-92.

Christodoulou AG, Shaw JL, Nguyen C, Yang Q, Xie Y, Wang N, et al. Magnetic resonance multitasking for motion-resolved quantitative cardiovascular imaging. Nature Biomedical Engineering. 2018;2(4):215-26.

Wang N, Gaddam S, Wang L, Xie Y, Fan Z, Yang W, et al. Six-dimensional quantitative Dce Mr Multitasking of the entire abdomen: Method and application to pancreatic ductal adenocarcinoma. Magn Reson Med. 2020;84(2):928-48.

Shaw JL, Yang Q, Zhou Z, Deng Z, Nguyen C, Li D, et al. Free-breathing, non-ECG, continuous myocardial T1 mapping with cardiovascular magnetic resonance Multitasking. Magn Reson Med. 2018.

Liang ZP. Spatiotemporal imaging with partially separable functions. In 2007 4th IEEE international symposium on biomedical imaging: from nano to macro Apr. 12, 2007 (pp. 988-991). IEEE.

Pedersen H, Kozerke S, Ringgaard S, Nehrke K, Kim WY. k-t PCA: temporally constrained k-t BLAST reconstruction using principal component analysis. Magn Reson Med. 2009;62(3):706-16.

Biswas S, Poddar S, Dasgupta S, Mudumbai R, Jacob M. Two step recovery of jointly sparse and low-rank matrices: Theoretical guarantees. In 2015 IEEE 12th International Symposium on Biomedical Imaging (ISBI) Apr. 16, 2015 (pp. 914-917). IEEE.

Christodoulou AG, Hitchens TK, Wu YL, Ho C, Liang ZP. Improved subspace estimation for low-rank model-based accelerated cardiac imaging. IEEE Trans Biomed Eng. 2014;61(9):2451-7.

Deng Z, Christodoulou AG, Wang N, Yang W, Wang L, Lao Y, Han F, Bi X, Sun B, Pandol SJ, Tuli R, Li D, Fan Z. Free-breathing volumetric body imaging for combined qualitative and quantitative tissue assessment using MR Multitasking. Proc Intl Soc Mag Reson Med, Montreal, 2019, #0698.

Tsao J, Boesiger P, Pruessmann KP. k-t BLAST and k-t SENSE: dynamic MRI with high frame rate exploiting spatiotemporal correlations. Magn Reson Med. 2003;50(5):1031-42.

Han F, Zhou Z, Cao M, Yang Y, Sheng K, Hu P. Respiratory motion-resolved, self-gated 4D-MRI using rotating cartesian k-space (ROCK). Med Phys. 2017;44(4):1359-68.

Otsu N. A threshold selection method from gray-level histograms. IEEE transactions on systems, man, and cybernetics. Jan. 1979;9(1):62-6.

Lo WC, Chen Y, Jiang Y, Hamilton J, Grimm R, Griswold M, Gulani V, Seiberlich N. Realistic 4D MRI abdominal phantom for the evaluation and comparison of acquisition and reconstruction techniques. Magn Reson Med. Mar. 2019;81(3):1863-75.

Chen J, Han P, Hu Z, Wang N, Yang W, Christodoulou AG, Li D, Fan Z. Multi-task MR simulation for abdominal radiation treatment planning: technical development. Proc Intl Soc Mag Reson Med, 2021, #4251.

Chen Y, Shaw JL, Xie Y, Li D, Christodoulou AG. Deep learning within a priori temporal feature spaces for large-scale dynamic MR image reconstruction: application to 5-D cardiac MR Multitasking. MICCAI 2019 (pp. 495-504).

Rieke V, Butts Pauly K. MR thermometry. Journal of Magnetic Resonance Imaging: An Official Journal of the International Society for Magnetic Resonance in Medicine. Feb. 2008;27(2):376-90.

Lagendijk JJ, Raaymakers BW, Van den Berg CA, Moerland MA, Philippens ME, Van Vulpen M. MR guidance in radiotherapy. Physics in Medicine & Biology. Oct. 16, 2014;59(21):R349.

Christodoulou AG, Shaw JL, Nguyen C, Yang Q, Xie Y, Wang N, Li D. Magnetic resonance multitasking for motion-resolved quantitative cardiovascular imaging. Nature biomedical engineering. Apr. 2018;2(4):215.

Feng L, Axel L, Chandarana H, Block KT, Sodickson DK, Otazo R. XD-GRASP: golden-angle radial MRI with reconstruction of extra motion-state dimensions using compressed sensing. Magnetic resonance in medicine. Feb. 2016;75(2):775-88.

Lingala SG, Hu Y, DiBella E, Jacob M. Accelerated dynamic MRI exploiting sparsity and low-rank structure: kt SLR. IEEE transactions on medical imaging. Jan. 31, 2011;30(5):1042-54.

Feng L, Otazo R. Magnetic Resonance SIGnature MAtching (MRSIGMA) for Real-Time Volumetric Motion Tracking. In Proceedings of the 27th Annual Meeting of ISMRM 2019 (p. 0578).

* cited by examiner

FIG. 7

SYSTEMS AND METHODS OF ON-THE-FLY GENERATION OF 3D DYNAMIC IMAGES USING A PRE-LEARNED SPATIAL SUBSPACE

CROSS REFERENCE TO RELATED APPLICATIONS

This application is a U.S. National Stage of International Application No. PCT/US2021/030667, filed May 4, 2021, which claims priority to and the benefit of U.S. Provisional Patent Application No. 63/019,791, filed May 4, 2020, each of which is hereby incorporated by reference herein in its entirety.

TECHNICAL FIELD

The present disclosure relates biomedical imaging and analysis. More specifically, the present disclosure relates to MRI image generation using a pre-learned spatial subspace.

BACKGROUND

Real-time magnetic resonance (MR) imaging is important in monitoring MR-based therapies and treatments. However, generating on-the-fly images with sufficient temporal resolution to track these therapies and treatments can be difficult. Due to the complexities involved, the generation of these on-the-fly images can be very slow. Thus, there is a need for new systems and methods that can more efficiently and rapidly construct on-the-fly MR images.

SUMMARY

According to aspects of the present disclosure, a method for performing magnetic resonance (MR) imaging on a subject comprises applying a first pulse sequence to a region of interest of the subject; in response to applying the first pulse sequence to the object, obtaining initial k-space data $D_1$; constructing a spatial factor $U_x$ and a temporal factor $\Phi$ from the initial k-space data $D_1$; determining a transformation T that maps the initial k-space data $D_1$ to the temporal factor $\Phi$; applying a second pulse sequence to the object; obtaining real-time k-space data $D_2$ at time t; and constructing a real-time image A, where $A=U_x TD_2$, real-time image A showing the region of interest of the subject at time t.

According to aspects of the present disclosure, a system for performing magnetic resonance (MR) imaging on a subject comprises a magnet operable to provide a magnetic field; a transmitter operable to transmit to a region within the magnetic field; a receiver operable to receive a magnetic resonance signal from the region with the magnetic field; and one or more processors operable to control the transmitter and the receiver, the one or more processors being configured to cause the following method to be performed: applying a first pulse sequence to a region of interest of the subject; in response to applying the first pulse sequence to the object, obtaining initial k-space data $D_1$; constructing a spatial factor $U_x$ and a temporal factor $\Phi$ from the initial k-space data $D_1$; determining a transformation T that maps the initial k-space data $D_1$ to the temporal factor $\Phi$; applying a second pulse sequence to the object; obtaining real-time k-space data $D_2$ at time t; and constructing a real-time image A, where $A=U_x TD_2$, real-time image A showing the region of interest of the subject at time t.

According to aspects of the present disclosure, a non-transitory machine-readable medium having stored thereon instructions for performing magnetic resonance (MR) imaging on a subject, which when executed by at least one processor, cause the following method to be performed: applying a first pulse sequence to a region of interest of the subject; in response to applying the first pulse sequence to the object, obtaining initial k-space data $D_1$; constructing a spatial factor $U_x$ and a temporal factor $\Phi$ from the initial k-space data $D_1$; determining a transformation T that maps the initial k-space data $D_1$ to the temporal factor $\Phi$; applying a second pulse sequence to the object; obtaining real-time k-space data $D_2$ at time t; and constructing a real-time image A, where $A=U_x TD_2$, real-time image A showing the region of interest of the subject at time t.

According to aspects of the present disclosure, a method for performing magnetic resonance (MR) imaging on a subject comprises obtaining a set of images of the subject; constructing a spatial factor $U_x$ and a temporal factor $\Phi$ from the set of images of the subject; determining a transformation T that maps k-space data to the temporal factor $\Phi$, the k-space data corresponding to the set of images; applying a pulse sequence to the object; obtaining real-time k-space data D at time t; and constructing a real-time image A, where $A=U_x TD$, real-time image A showing the region of interest of the subject at time t.

According to aspects of the present disclosure, a system for performing magnetic resonance (MR) imaging on a subject comprises a magnet operable to provide a magnetic field; a transmitter operable to transmit to a region within the magnetic field; a receiver operable to receive a magnetic resonance signal from the region with the magnetic field; and one or more processors operable to control the transmitter and the receiver, the one or more processors being configured to cause the following method to be performed: obtaining a set of images of the subject; constructing a spatial factor $U_x$ and a temporal factor $\Phi$ from the set of images of the subject; determining a transformation T that maps k-space data to the temporal factor $\Phi$, the k-space data corresponding to the set of images; applying a pulse sequence to the object; obtaining real-time k-space data D at time t; and constructing a real-time image A, where $A=U_x TD$, real-time image A showing the region of interest of the subject at time t.

According to aspects of the present disclosure, a non-transitory machine-readable medium having stored thereon instructions for performing magnetic resonance (MR) imaging on a subject, which when executed by at least one processor, cause the following method to be performed: obtaining a set of images of the subject; constructing a spatial factor $U_x$ and a temporal factor $\Phi$ from the set of images of the subject; determining a transformation T that maps k-space data to the temporal factor $\Phi$, the k-space data corresponding to the set of images; applying a pulse sequence to the object; obtaining real-time k-space data D at time t; and constructing a real-time image A, where $A=U_x TD$, real-time image A showing the region of interest of the subject at time t.

The foregoing and additional aspects and implementations of the present disclosure will be apparent to those of ordinary skill in the art in view of the detailed description of various embodiments and/or implementations, which is made with reference to the drawings, a brief description of which is provided next.

BRIEF DESCRIPTION OF THE DRAWINGS

The foregoing and other advantages of the present disclosure will become apparent upon reading the following detailed description and upon reference to the drawings.

While the present disclosure is susceptible to various modifications and alternative forms, specific implementations and embodiments have been shown by way of example in the drawings and will be described in detail herein. It should be understood, however, that the present disclosure is not intended to be limited to the particular forms disclosed. Rather, the present disclosure is to cover all modifications, equivalents, and alternatives falling within the spirit and scope of the present disclosure as defined by the appended claims.

DETAILED DESCRIPTION

While the present disclosure has been described with reference to one or more particular embodiments or implementations, those skilled in the art will recognize that many changes may be made thereto without departing from the spirit and scope of the present disclosure. Each of these embodiments or implementations and obvious variations thereof is contemplated as falling within the spirit and scope of the present disclosure. It is also contemplated that additional embodiments implementations according to aspects of the present disclosure may combine any number of features from any of the embodiments or implementations described herein.

Magnetic resonance-based imaging (MR imaging) is a technique most often used for imaging the human body that takes into account principles of nuclear magnetic resonance. For example, doctors and other medical professionals often use MR imaging to view tissue within the human body. Nuclear magnetic resonance is a phenomenon in which nuclei (such as protons in body tissue) localized in a magnetic field emit energy that can be detected. This energy that is detected can be used to create an image. MR imaging generally involves two principle steps. First, the magnetic moment of the nuclei (a vector property of a nucleus caused by the intrinsic spin property of elementary particles) are aligned (or polarized) by the presence of an external magnetic field. While in the presence of this external magnetic field, the magnetic moment of each nuclei will generally precess about an axis parallel to the magnetic field. The rate of this precession $\omega$ is generally proportional to $\gamma B_0$, where $B_0$ is the magnitude of the external magnetic field, and $\gamma$ is the gyromagnetic ratio of the nuclei, which is the ratio the nuclei's magnetic moment to its angular momentum. The rate of the precession $\omega$ is considered the nuclei's resonant frequency.

The second principle step in MR imaging is to apply an electromagnetic pulse sequence (usually a radiofrequency, or RF, pulse) to the nuclei. When the frequency of the RF pulses sequence is generally equal to the resonant frequency of the nuclei, the nuclei absorb the energy of the RF pulse and the magnetic moments are rotated out of alignment with the magnetic field. The magnetic moments of the excited nuclei eventually re-align within the presence of the external magnetic field in a process known as relaxation, which has two components, $T_1$ and $T_2$. $T_1$ relaxation describes how the component of the magnetic moment parallel to the external magnetic field returns to its initial value. $T_2$ relaxation describes how the components of the magnetic moment perpendicular to the external magnetic field return to their initial value. Because the magnetic moments of nuclei in the external magnetic field without the RF pulse sequence applied are generally parallel to the external magnetic field, $T_1$ relaxation generally describes how parallel component of the magnetic moment returns to its maximum value, while $T_2$ relaxation generally describes how the perpendicular components of the magnetic moment decay. The nuclei of different material relax at different rates and thus emit differing signals, which can be detected and used to form an image identifying the different materials.

Dynamic MR imaging can produce a spatiotemporal image sequence I(x, t), which is a function of (i) spatial location within the subject and (ii) one or more time-varying parameters related to the dynamic processes. The spatial location is denoted by vector $x=[x_1, x_2, x_3]^T$, which contains up to three spatially-varying parameters $x_i$. The time-varying parameters are denoted by vector $t=[t_1, t_2, \ldots, t_R]^T$ containing R time-varying independent variables $t_i$. The imaging data obtained from the MR imaging is generally from a specific region of interest of the subject. In an example, the region of interest could be the subject's abdomen or chest. In other examples, the region of interest of the subject is more specific. For example, the region of interest could be an organ, such as the subject's liver, lungs, heart, pancreas, brain, prostate, breast, or any other organ.

The imaging data is dependent on or related to the spatially-varying and time-varying parameters of the region of interest of the subject referred to above. The spatially-varying parameters include a voxel location, a contrast agent kinetic parameter, or a diffusion parameter (which includes changing strength, changing direction, or both). The spatially-varying parameters can additionally or alternatively be related to physical motion of the region of interest of the subject. The time-varying parameters can include, but is not limited to: the phase of the subject's heart within a cardiac cycle; the position of the subject's lungs, chest wall, or other organs within a respiratory cycle; a position of a dome of a liver during respiration; relaxation parameters such as T1, T1ρ (also known as T1-rho), T2, T2* (also known as T2-star), an inversion time (or other time since magnetization preparation); a diffusion weighting strength; a diffusion weighting direction; an echo time; a dynamic contrast enhancement phase; a flip angle; an elapsed time since the start of scanning; elastographic wave propagation, a phase offset of elastographic excitation waves; a frequency offset and duration of saturation preparation pulses (e.g., for chemical exchange saturation transfer); a duration of magnetization transfer preparation pulses; a chemical exchange saturation transfer, a spectral position (e.g., for spectroscopy); a flow encoding strength; a flow encoding direction; free induction decay, or the general passage of time.

Some of the spatially-varying parameters can also be time-varying, and some of the time-varying parameters can also be spatially-varying. For example, cardiac motion is generally a time-varying parameter, while the relaxation parameters, the contrast agent kinetic parameter, and the diffusion parameter are generally time-varying. Generally, the imaging data is indicative of the value or magnitude of the spatially-varying parameters and/or the time-varying parameters. In another example, the region of interest is the subject's abdomen containing their liver, and the spatially-varying parameter that is being measured is the $T_1$ relaxation parameter. The $T_1$ relaxation parameter can be spatially-varying, meaning that the value of the $T_1$ relaxation parameter at a first physical location within the subject's liver can be different than the value of the $T_1$ relaxation parameter at a second physical location within the subject's liver. In a resulting image showing the value measured $T_1$ relaxation parameter, different locations in the image (corresponding to different physical locations within the subject's liver) will show different values. In some implementations, the spatially-varying parameters can also be time-varying. In other implementations, the spatially-varying parameters can additionally or alternatively be related to physical motion of the region of interest of the subject. In general, the techniques disclosed herein can be used to perform dynamic imaging that resolves parameters that can vary across space and time.

The image sequence $I(x, t)$ can be represented as a matrix A:

$$A = \begin{bmatrix} a(x_1, t_1) & \cdots & a(x_1, t_{N_t}) \\ \vdots & \ddots & \vdots \\ a(x_J, t_1) & \cdots & a(x_J, t_{N_t}) \end{bmatrix}$$

Matrix A can be decomposed as:

$$A = U_x \Phi = \begin{bmatrix} | & & | \\ u_1 & \cdots & u_L \\ | & & | \end{bmatrix} \begin{bmatrix} -\phi_1- \\ \vdots \\ -\phi_L- \end{bmatrix}$$

In this formulation, J is the total number of voxels in the image, and $N_t$ is the number of time points. $U_x \in C^{J \times L}$ contains L spatial basis functions with J total voxels and is known as a spatial factor. $U_x$ contains one or more spatial basis functions that describe the properties of the spatially-varying parameters. $U_x$ is formed as a spatial factor matrix. $\Phi \in C^{L \times N_t}$ contains temporal weighting functions, and is known as the temporal factor. The weighting functions describe properties of time-varying parameters, such as relaxation, motion, contrast changes, etc. $\Phi$ is formed as a temporal factor matrix where imaging with only a single time dimension is used, and is formed as a temporal factor tensor where imaging with multiple time dimensions is used.

Figure 1:
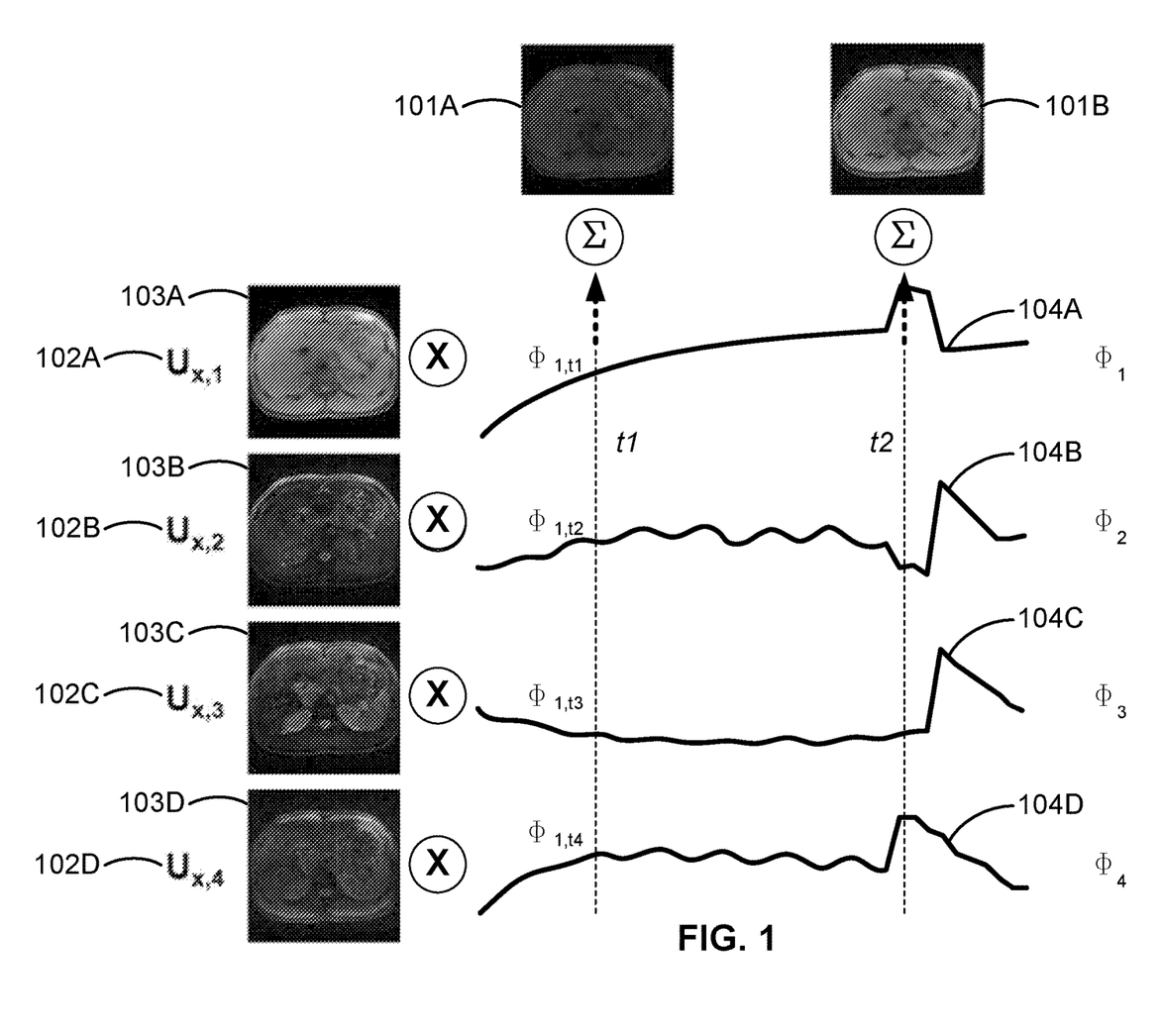
FIG. 1 shows images being constructed as linear combination of spatial basis functions weighted by temporal basis functions, according to aspects of the present disclosure.

Referring now to FIG. 1, at a specific point in time $t=t_s$, the real-time image $a_{t_s}$ can be expressed as a linear combination of the spatial basis functions, weighted by the vector $\phi_{t_s} = (\phi_{1,t_s}, \ldots, \phi_{L,t_s})^T$:

$$a_{t_s} = \begin{bmatrix} a(x_1, t_s) \\ \vdots \\ a(x_J, t_s) \end{bmatrix} = \phi_{1,t_s} \begin{bmatrix} | \\ u_1 \\ | \end{bmatrix} + \ldots + \phi_{L,t_s} \begin{bmatrix} | \\ u_L \\ | \end{bmatrix} = \sum_{i=1}^{L} \phi_{i,t_s} u_i.$$

$\phi_{t_s}$ is the column of $\Phi$ corresponding to time point $t_s$. FIG. 1 shows two images 101A and 101AB that are combinations of four different spatial basis functions 102A, 102B, 102C, and 102D (denoted as $U_{x,1}$, $U_{x,2}$, $U_{x,3}$, and $U_{x,4}$), weighted by four different temporal weighting functions 104A, 104B, 104C, and 104D (denoted as $\phi_1$, $\phi_2$, $\phi_3$, and $\phi_4$). Image 101A is produced at time $t_1$, while image 101B is produced at time $t_2$. As is shown, each spatial basis function 102A-102D can be used to produce a corresponding sub-image 103A-103D. Spatial basis function 102A is weighted less by temporal basis function 104A relative to the other spatial basis functions at time $t_1$ as compared to time $t_2$. Thus, spatial basis function 102A (e.g., corresponding sub-image 103A) contributes less to image 101A than it does to image 101B. Image 101B thus bears more resemblance to sub-image 103A than it does sub-image 101A. The sub-images 103B and 103D contribute relatively more to image 101 than they do image 101B. The sub-image 103C contributes relatively similar amounts to images 101 and 101B.

Figure 2:
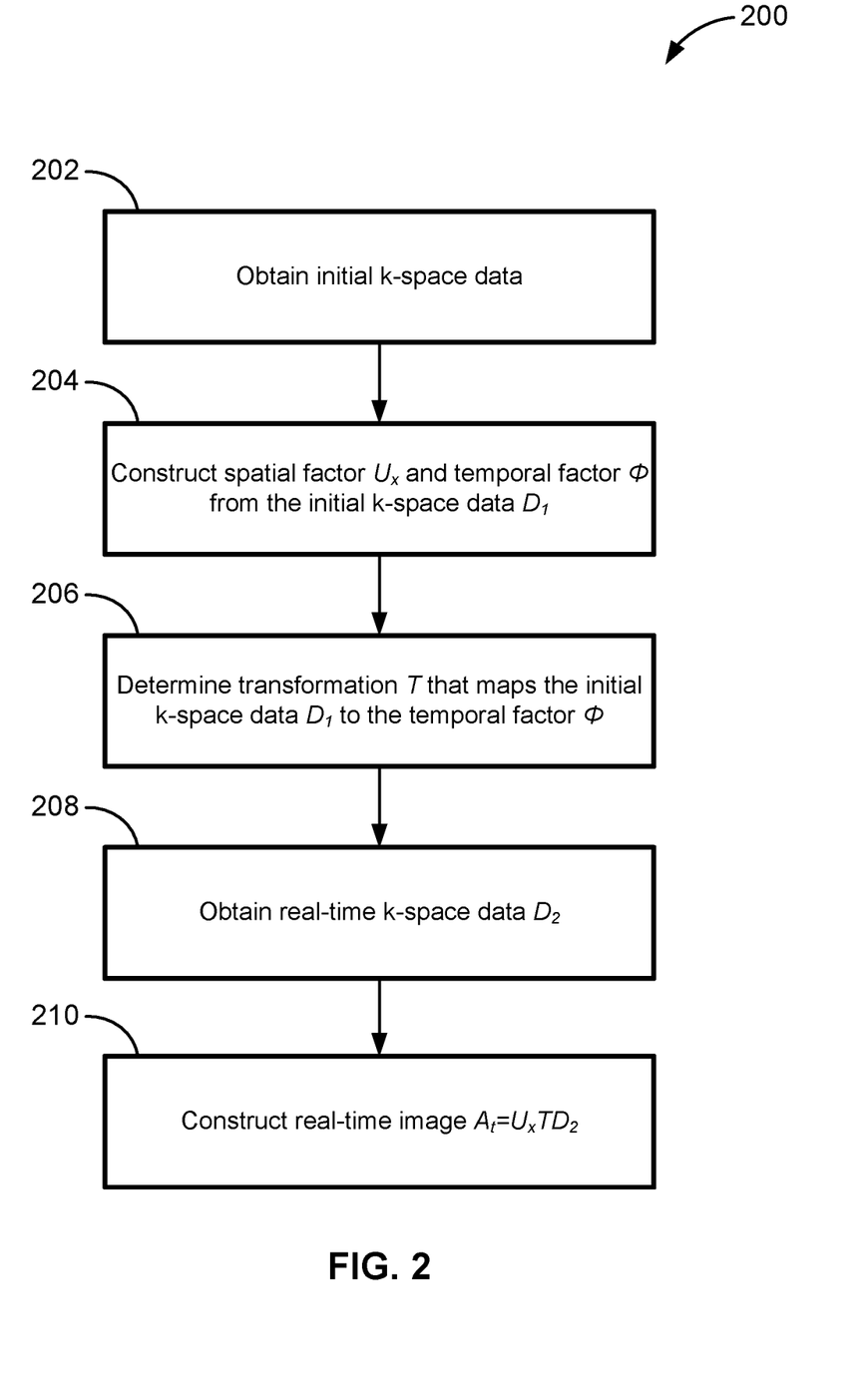
FIG. 2 shows a method for performing magnetic resonance imaging on a subject, according to aspects of the present disclosure.

Referring now to FIG. 2, a method 200 for performing real-time MR imaging on a subject of interest is illustrated. Real-time MR imaging is an MR imaging technique that is useful for MR guided therapies and interventions. In normal MR imaging, so long as the scan time is sufficiently short so that they subject can remain still for the entire scan, other considerations are relatively more important than the total scan time and total time to obtain the images. The desired images can be reconstructed after the scan is complete. However, during MR guided therapies and interventions, it is important to be able to generate on-the-fly images so as to visually track the progress of the therapy or intervention.

At step 202, initial k-space data $D_1$ is obtained by applying a first pulse sequence to a region of interest of the subject. Generally, the first pulse sequence will be a "prep" pulse sequence, that is not actually used to create any images. The initial k-space data $D_1$ includes both training data $D_{tr}$ (sometimes referred to as navigator data) and imaging data $D_{im}$. The training data $D_{tr}$ is data sampled frequently at a limited number of k-space locations, such as the central part of the k-space. The imaging data $D_{im}$ is data acquired from the entire-space with appropriate sampling scheme, such as randomized Cartesian or golden-angle radial trajectories.

At step 204, spatial factor $U_x$ and temporal factor $\Phi$ are obtained from the initial k-space data $D_1$. In some implementations, the temporal factor Φ is constructed from only the training data $D_{tr}$. In other implementations, the temporal factor Φ is constructed from both the training data $D_{tr}$ and the imaging data $D_{im}$. The spatial factor $U_x$ can be reconstructed by solving the following problem:

$$\hat{U}_x = \operatorname{argmin}_{U_x} \|D_{im} - \Omega(EU_x\Phi)\|_2^2 + \lambda R(U_x).$$

Here, E is the signal encoding operator, Ω is the k-space undersampling operator, and R is the regularization function to explant compressed sensing.

At step 206, a transformation T is determined that maps the initial k-space data $D_1$ to the temporal factor Φ. Because Φ are the temporal weights of $U_x$, any image can be generated according to $A = U_x TD$, where D is k-space data obtained during the MR scan. Thus, with respect to the first pulse sequence, $\Phi = TD_{tr}$, where T is a linear transform given by $T \in \mathbb{C}^{L \times M}$ that maps the training data $D_{tr}$ to the temporal factor Φ. For an individual time point $t = t_s$, the training data $d_{tr,t_s} \in \mathbb{C}^{M \times 1}$ can be transformed into $\phi_{t_s}$ with $\phi_{t_s} = Td_{tr,t_s}$. Accordingly, the entire 3D image at $t = t_s$ can be generated with a simple matrix multiplication:

$$a_{t_s} = U_x \phi_{t_s} = U_x T d_{tr,t_s}.$$

In a long scan with periodic signal evolution, the spatial factor $U_x$ and the transformation T should remain static during the acquisition process, unless abrupt body motion or unexpectedly-introduced contrast mechanisms force the new images outside the range of $U_x$. Thus, T can be determined using only the first pulse sequence (e.g., the prep pulse sequence), according to the following equation: $\hat{T} = D_{tr}^+ \Phi$. Here, $D_{tr}^+$ is the pseudo-inverse of $D_{tr}$. By determining the spatial factor $U_x$, a pre-learned spatial subspace is obtained. By determining the transformation T, the pre-learned spatial subspace can then be used during real-time imaging. In some implementations, the pre-learned spatial subspace can have contributions from different image contrasts, such as T1-weighting, T2-weighting, or proton density-weighting.

At step 208, real-time k-space data $D_2$ is obtained by applying a second pulse sequence to the region of interest of the subject. Generally, the real-time k-space data $D_2$ can be just real-time training data, e.g., a single k-space line or trajectory.

Finally, at step 210, a real time image A of the region of interest of the subject is constructed at time t, where $A = U_x TD_2$. Because $U_x$ and T were determined from the first pulse sequence applied to the subject (e.g., the prep pulse sequence), and because $U_x$ and T remain unchanged throughout data acquisition in the absence of abrupt movement and unexpectedly-introduce contrast mechanisms, real-time images can quickly be generated during a live scan simply by acquiring the real-time k-space data $D_2$. In implementations where the real-time k-space data $D_2$ is only training data obtained at time $t = t_s$, the notation $D_{:,t_s}$ is used for the real-time k-space data, and thus the real-time image given by $A_{:,t_s} = U_x TD_{:,t_s}$, where $A_{:,t_s}$ is constructed from only real-time training data. In some implementations, $A_{:,t_s}$ is obtained using a fast matrix multiplication procedure.

When the above method is used for non-steady-state sequences with periodic signal evaluation, such as sequences with inversion recovery, saturation recovery, or T2 preparation modules, the temporal factor Φ contains the information not only about respiratory motion, but also contrast changes. In retrospective reconstruction, the raw data sampled at different motion states and different time points along the signal recovery curve can be grouped into different bins to generate images along one specific time dimension. Similarly, there is also a need during the second pulse sequence to separate the motion information and contrast information, so that real-time images can be displayed with a stable contrast, e.g., T1 weighted (T1w), T2 weighted (T2w), or proton density weighted (PDw), while maintaining the true motion state. This can be achieved by projecting real-time temporal factor Φ onto Bloch-simulated subspaces of different contrasts. First, an auxiliary temporal factor $\Phi_{Bloch}$ is generated from the singular value decomposition of a Bloch simulated training dictionary, based on the sequence structure. It contains the information only about contrast change. Second, the temporal factor Φ learned from the first pulse sequence is projected onto $\Phi_{Bloch}$. This gives $\Phi_{cc}$, the "contrast change" part of Φ: $\Phi_{cc} = \Phi \Phi_{Bloch}^+ \Phi_{Bloch}$, where $\Phi_{Bloch}^+$ is the pseudo-inverse of $\Phi_{Bloch}$.

Last, the image contrast at any time $t = t_c$ can be synthesized in the second pulse sequence scan by replacing $\phi_{t_s}$ with $\tilde{\phi}_{t_s}(t_c) : \tilde{\phi}_{t_s}(t_c) = \phi_{t_s} + \Delta\phi_{cc,t_s}(t_c)$, where $\Delta\phi_{cc,t_s}(t_c) = \phi_{cc,t_c} - \phi_{cc,t_s}$ denotes the contrast adjustment term, and $t_c$ refers to the time point with the contrast of interest, e.g., T1w, T2w, or PDw. Thus, for contrast-frozen, motion-maintained real-time imaging, the entire 3D image can be generated as follows:

$$a_{t_s}(t_c) = U_x \tilde{\phi}_{t_s}(t_c) = U_x(TD_{2,t_s} + \Delta\phi_{cc,t_s}(t_c))$$

By using a sequence in which multiple image contrasts present along the signal evolution, multi-contrast real-time images can be generated using several different $t_c$'s pointing at different image contrasts.

In some implementations, there is bulk motion during the scan. The bulk motion can be the result of the subject moving during the can, but can have other causes. In these implementations, differences between $D_1$ and $D_2$ can be detected, and $U_x$ can be updated before applying transformation T. For example, a 1 millimeter bulk motion shift can be detected and corrected for.

In some implementations, the real-time k-space data $D_{:,t_s}$ is obtained within a time period of about 4 milliseconds, and the real-time image $A_{:,t_s}$ is constructed within a time period of about 40 milliseconds (e.g., the elapsed time to transform the training data readout readout $D_{:,t_s}$ and weight the spatial basis $U_x$ is about 40 milliseconds). Thus, the real-time image $A_{:,t_s}$ can have a temporal resolution of about 50 milliseconds or less. If the pre-learned spatial subspace has a specific contrast weighting, contrast-variated real-time images can be transferred onto contrast-frozen images maintaining the true motion state. Moreover, because method 200 is capable of reconstructing any image along a continuum within the pre-learned spatial subspace, method 200 does not rely on binning to select an image from a discrete dictionary of potential results, and supports multi-contrast imaging.

Figure 3:
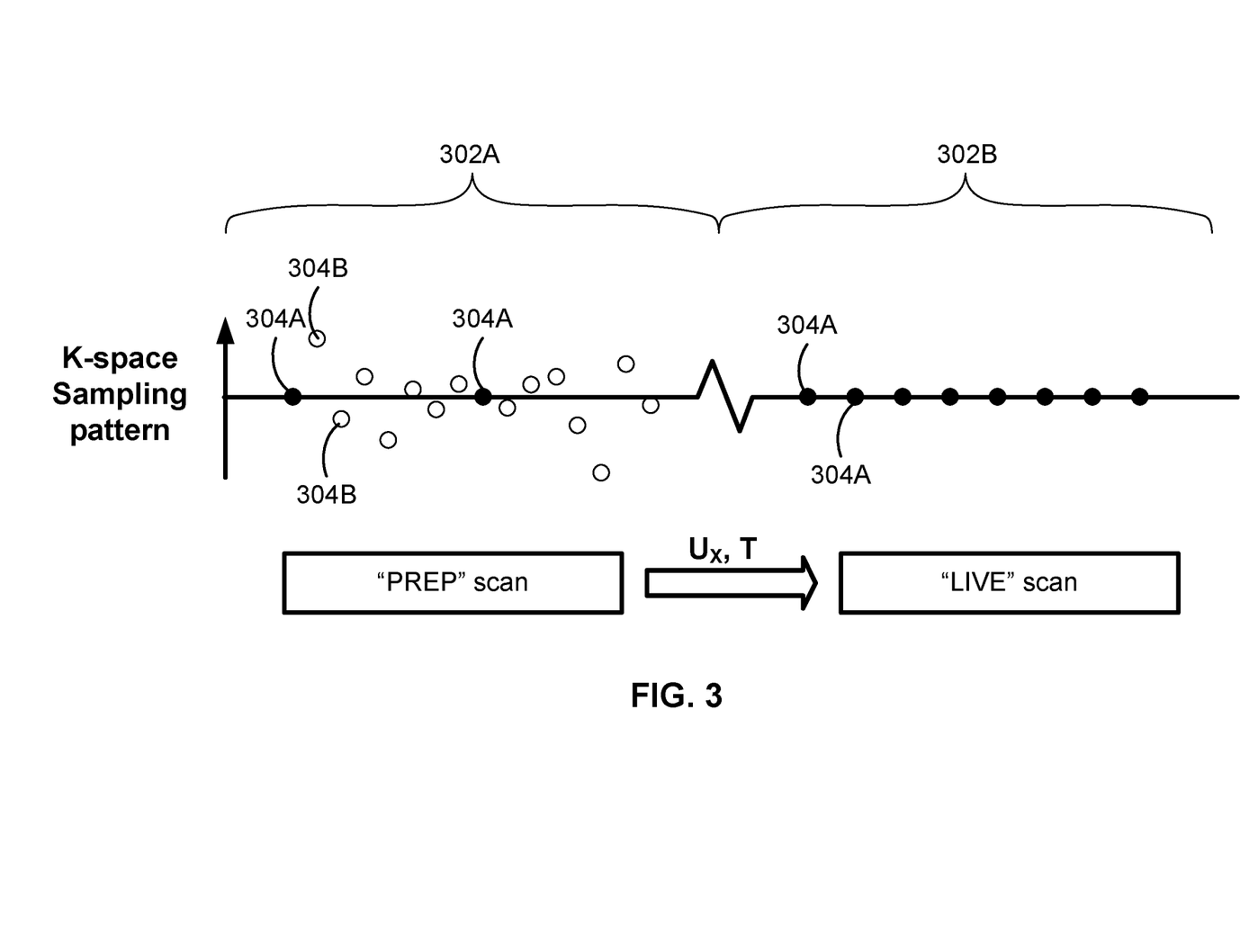
FIG. 3 shows an example k-space sampling pattern for use with the method of FIG. 2, according to aspects of the present disclosure.

FIG. 3 shows an example k-space sampling pattern that includes both the first pulse sequence 302A and the second pulse sequence 302B. As is shown, the first pulse sequence 302A includes both training data 304A and imaging data 304B, from which $U_x$ and T can be obtained. The second pulse sequence 302A includes only training data 304A, from which the real-time image $A_{:,t_s}$ can be constructed.

Figure 4A:
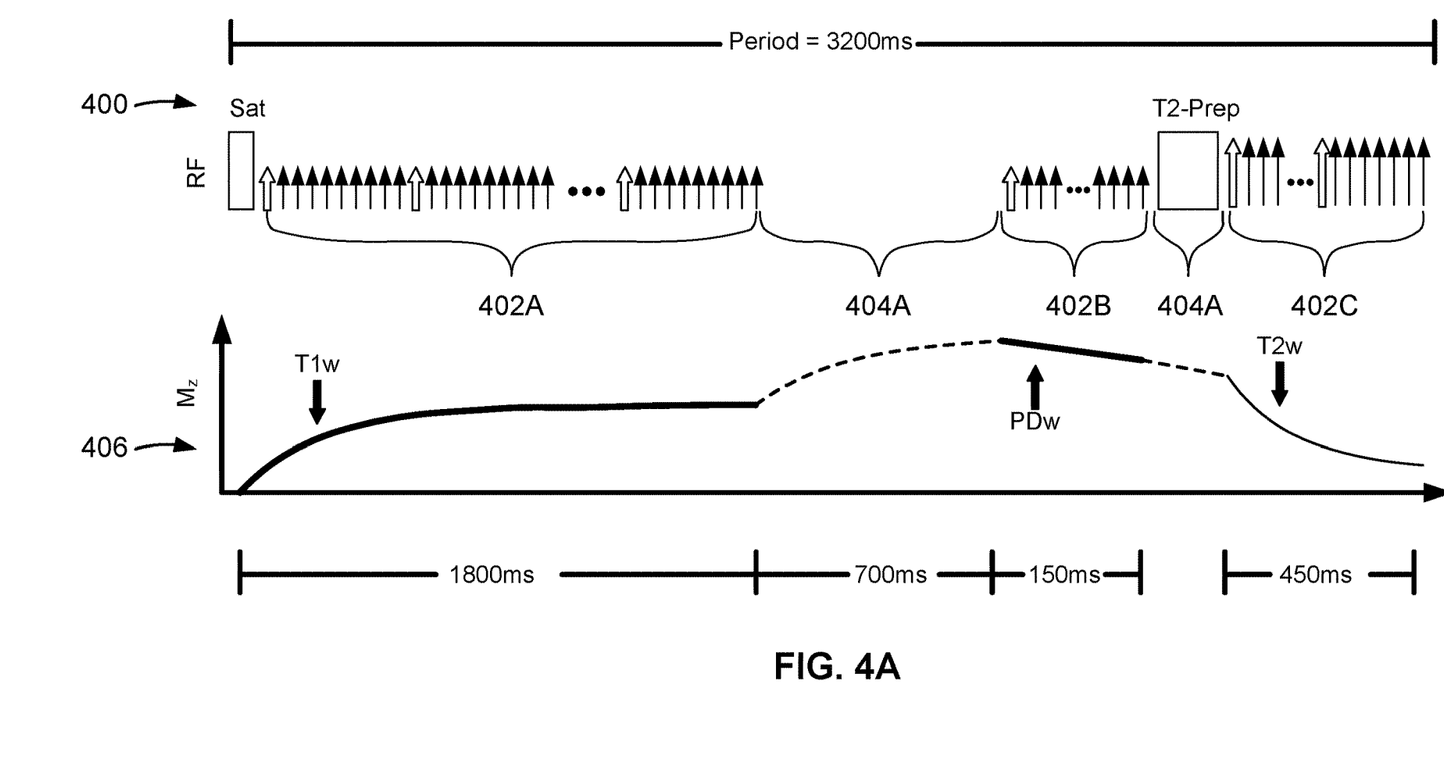
FIG. 4A shows an example pulse sequence for use with the method of FIG. 2, according to aspects of the present disclosure.
Figure 4B:
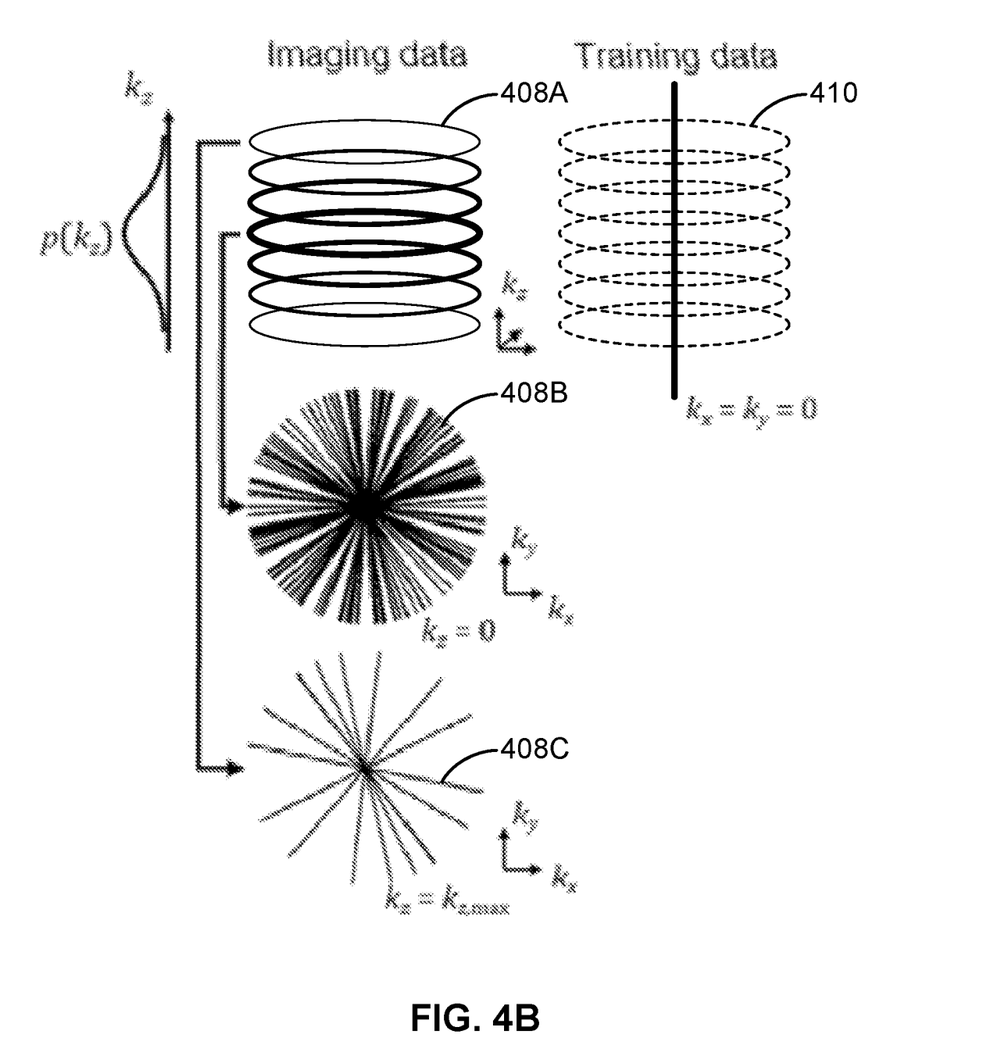
FIG. 4B shows the k-space representations of training data and imaging data obtained using the example pulse sequence of FIG. 4A, according to aspects of the present disclosure.

FIG. 4A shows an example pulse sequence 400 that can be used with method 200 illustrated in FIG. 2. With pulse sequence 400, k-space is continuously sampled using a stack-of-stars gradient echo (GRE) sequence. The pulse sequence 400 has golden angle ordering in the x-y plane and Gaussian-density randomized ordering in the z-direction, and is interleaved with training data (0° in-plane, central partition) every tenth readout. Saturation recovery (SR) preparation and T2 preparation are combined to generated T1-weighted and T2-weighted signals during magnetization evolution. As shown, the pulse sequence generally includes a first portion 402A corresponding to T1-weighting (lasting about 1,800 ms), a second portion corresponding to proton-density weighting 402B (lasting about 150 ms), a third portion corresponding to T2-weighting (lasting about 450 ms), a first gap 404A between the first portion 402A and the second portion 402B (lasting about 700 ms), and a second gap between the second portion 402B and the third portion 404C (lasting about 100 ms) that corresponds to a T2-prep cycle. The entire pulse sequence lasts about 3,200 ms. In one example, the following parameters can be used for abdominal T1/T2 multitasking with the example pulse sequence 400: matrix size=160×160×52; field of view=275×275×240 mm$^3$; voxel size=1.7×1.7×6 mm$^3$; TR/TE=6.0/2.1 milliseconds; flip angle=5° following saturation recovery preparation; flip angle=10° following T2 preparation; water-excitation for fat suppression; and a total imaging time of approximately eight minutes. FIG. 4B also shows a plot 406 representing the magnetization in the z-direction during the pulse sequence.

FIG. 4B shows the k-space representations of the imaging data and the training data obtained using pulse sequence 400. To obtain the imaging data, the k-space can be continuously sampled with a FLASH readout using a stack-of-stars acquisition with golden angle ordering in the x-y plane (408A and 408B), and Gaussian-density randomized ordering in the z-direction (408C). To obtain the training data, the k-space can be sampled as a central line along the z-direction, with $k_x=k_y=0$ (410).

While FIGS. 4A and 4B shows a stack-of-stars acquisition scheme, many other acquisition schemes can be used in conjunction with method 200 and the pulse sequences 302A and 302B. Potential acquisition schemes includes stack-of-stars, Cartesian, three-dimensional (3D) radial, spiral, stack-of-spirals, and echoplanar.

Figure 5A:
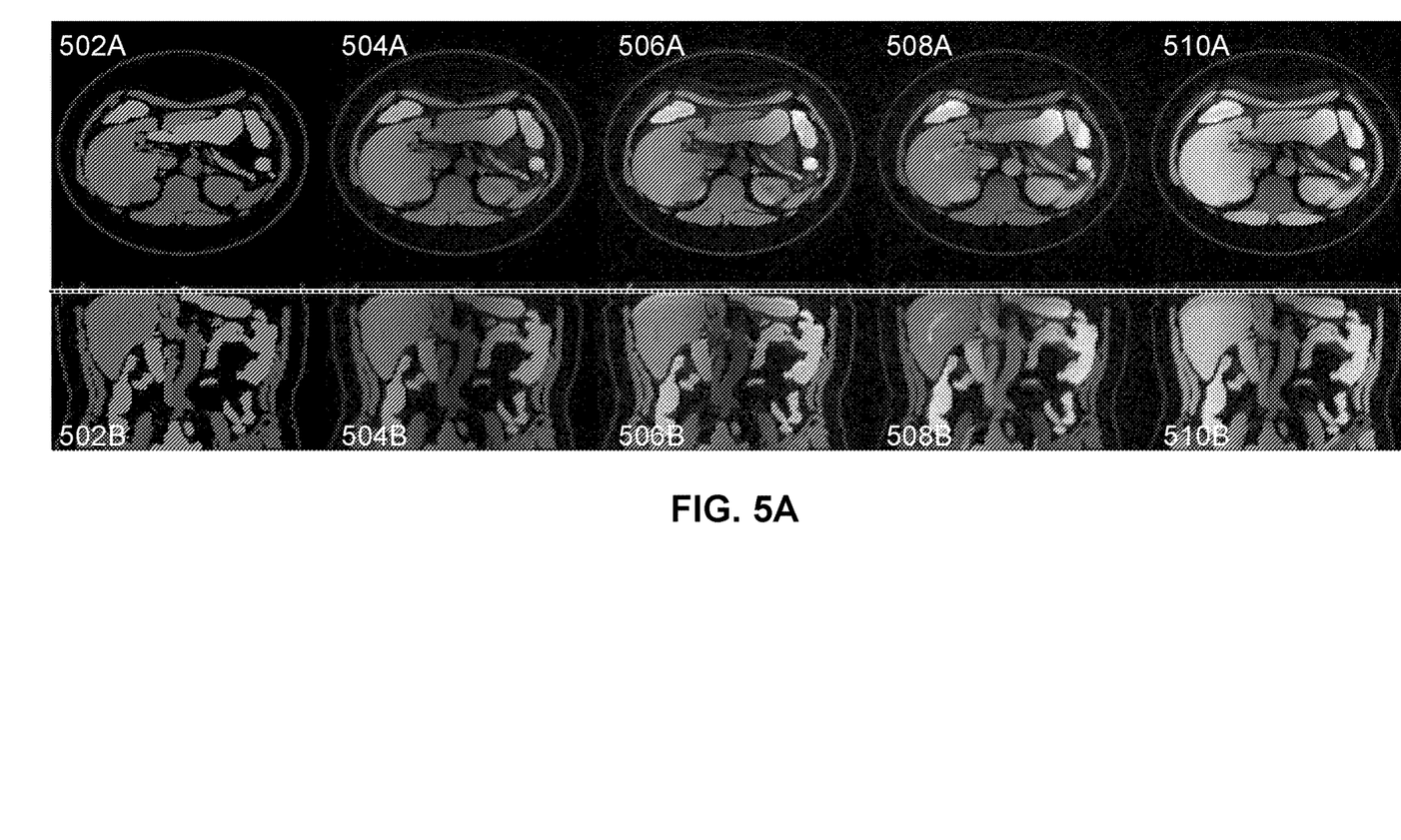
FIG. 5A shows a first comparison between reference abdominal images at end-expiration (top and front) that are contrast-variated, and real-time abdominal images at end-expiration (top and front) that are contrast-variated, T1-weighted, T2-weighed, and proton density (PD)-weighted, according to aspects of the present disclosure.
Figure 5B:
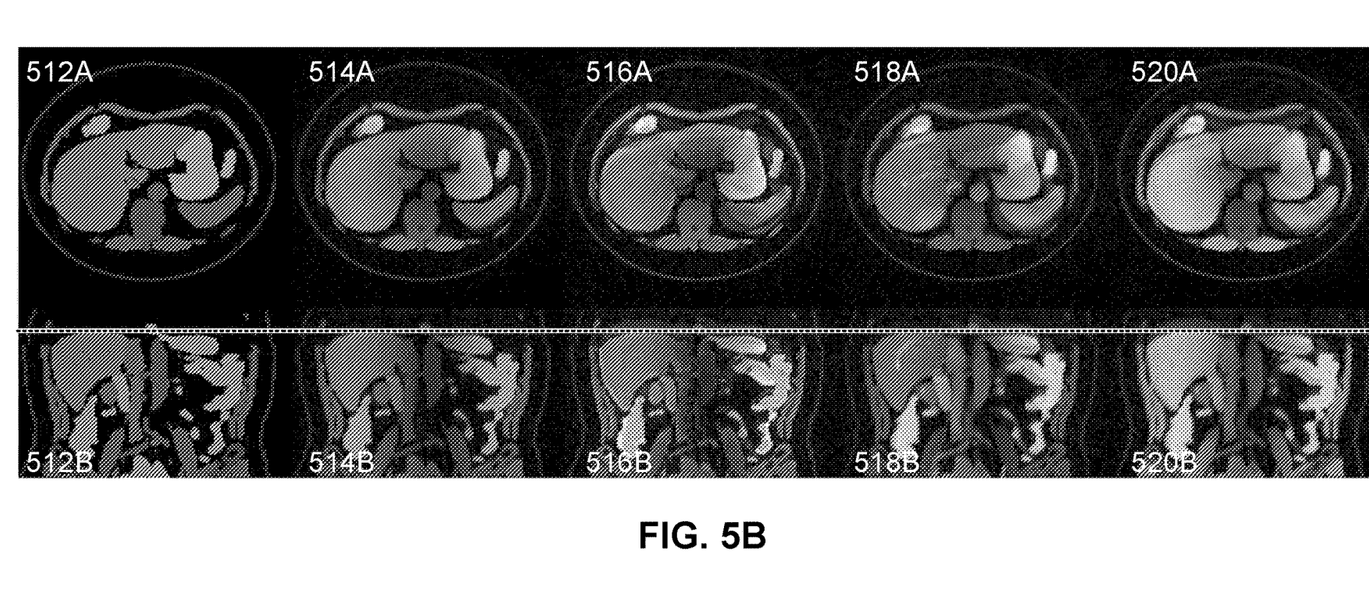
FIG. 5B shows a first comparison between reference abdominal images at end-inspiration (top and front) that are contrast-variated, and real-time abdominal images at end-inspiration (top and front) that are contrast-variated, T1-weighted, T2-weighed, and proton density (PD)-weighted, according to aspects of the present disclosure.

FIGS. 5A and 5B shows MR images that compare reference images with real-time images using the techniques disclosed herein. The images were obtained by imaging digital phantoms. First, k-space data of about 60,000 time points (corresponding to a total scan time of about 8 minutes) was obtained using the sampling pattern of FIGS. 4A and 4B. The images have a matrix size of 320×320×52, and a voxel size of 1.7×1.7×4.9 mm$^3$. Time-varying breathing patterns were simulated with interleaved pseudo-randomized normal (~4.2 sec), long (~6.3 sec) and short (~3.2 sec) respiratory cycles. For normal cycles, the largest excursion along superior-inferior (SI), anterior-posterior (AP) and left-right (LR) direction was 13 mm, 6.5 mm, and 2 mm, respectively. The 60,000-point data was viewed as the first pulse sequence (e.g., the prep scan, from which the spatial factor $U_x$, the linear transformation T, and the contrast-change part of $\Phi$, $\Phi_{cc}$, were generated. Then, 100 time points of training data were simulated with different motion positions and contrasts. This data was viewed as a demo first pulse sequence and processed with the techniques disclosed herein to generate multi-contrast 3D images that were compared with true reference images of the phantom.

The images in FIG. 5A are top and front images of an abdomen at end expiration, while the images in FIG. 5B are top and front images of an abdomen at end inspiration. FIG. 5A includes reference images 502A (top) and 502B (front). Real-time images 504A (top) and 504B (front) are contrast-variated images generated using the techniques disclosed herein. Real-time images 506A (top) and 506B (front) are T1-weighted frozen images generated using the techniques disclosed herein. Real-time images 508A (top) and 508B (front) are T2-weighted frozen images generated using the techniques disclosed herein. Real-time images 510A (top) and 510B (front) are PD-weighted frozen images generated using the techniques disclosed herein. FIG. 5B includes reference images 512A (top) and 512B (front). Real-time images 514A (top) and 514B (front) are contrast-variated images generated using the techniques disclosed herein. Real-time images 516A (top) and 516B (front) are T1-weighted frozen images generated using the techniques disclosed herein. Real-time images 518A (top) and 518B (front) are T2-weighted frozen images generated using the techniques disclosed herein. Real-time images 520A (top) and 520B (front) are PD-weighted frozen images generated using the techniques disclosed herein. The dotted lines in the front images (lower row) of FIG. 5A and FIG. 5B indicate that the respiratory position in the real-time images obtained using techniques disclosed herein is consistent with the respiratory position in the reference images. Thus, the real-time images obtained using conventional techniques show consistent motion displacement with the reference images.

Figure 6A:
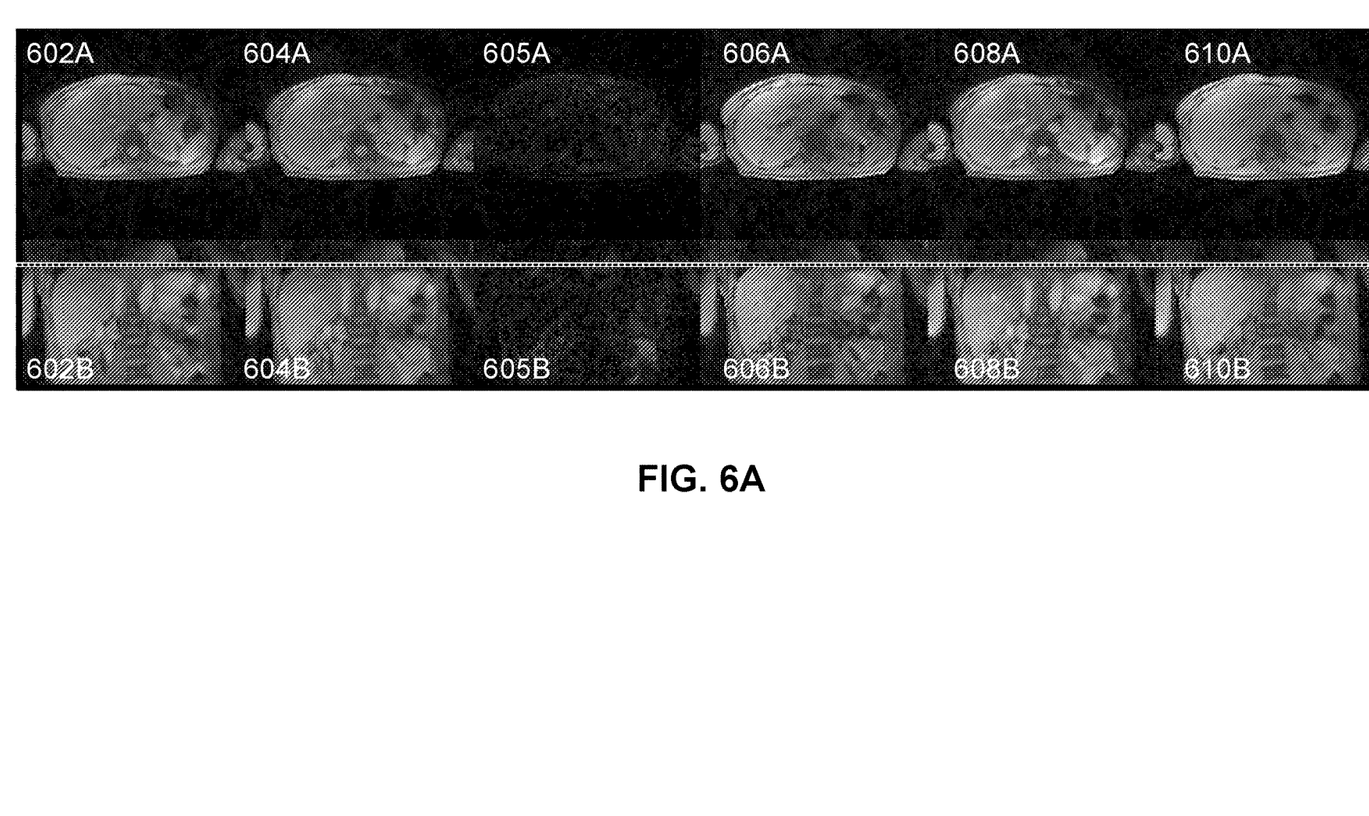
FIG. 6A shows a second comparison between reference abdominal images at end-expiration (top and front) that are contrast-variated, and real-time abdominal images at end-expiration (top and front) that are contrast-variated, T1-weighted, T2-weighed, and proton density (PD)-weighted, according to aspects of the present disclosure.
Figure 6B:
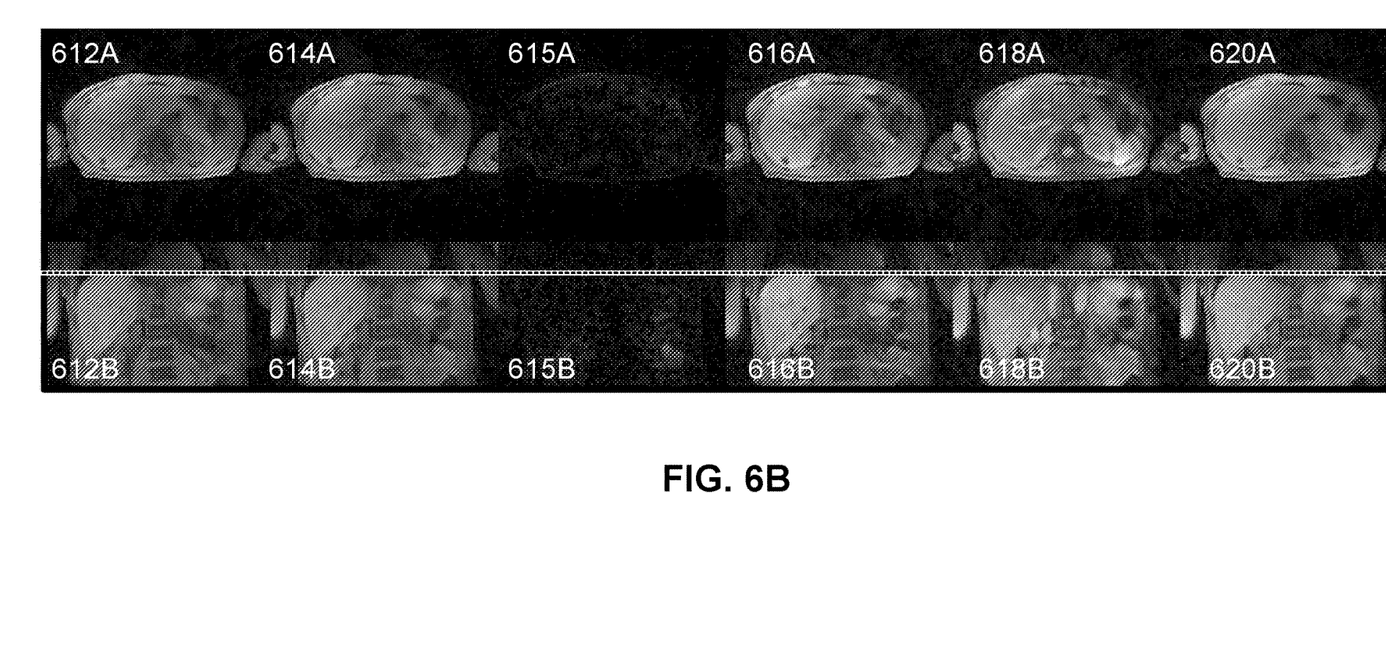
FIG. 6B shows a second comparison between reference abdominal images at end-inspiration (top and front) that are contrast-variated, and real-time abdominal images at end-inspiration (top and front) that are contrast-variated, T1-weighted, T2-weighed, and proton density (PD)-weighted, according to aspects of the present disclosure.

FIGS. 6A and 6B shows MR images that compare reference images with real-time images using the techniques disclosed herein. The images were obtained by imaging seven healthy subjects on a 3.0 T clinical scanner equipped with an 18-channel phase array body coil. For each subject, two identical scans were performed successively, serving as the first pulse sequence and the second pulse sequence. The first pulse sequence was used to learn and stored the spatial factor $U_x$, the linear transformation T, and the contrast-change part of $\Phi$, $\Phi_{cc}$.

The images in FIG. 6A are top and front images of an abdomen at end expiration, while the images in FIG. 6B are top and front images of an abdomen at end inspiration. FIG. 6A includes reference images 602A (top) and 602B (front). Real-time images 604A (top) and 604B (front) are contrast-variated images generated using the techniques disclosed herein. Images 605A (top) and 605B (front) show the difference between reference images 602A and 602B, and real-time images 604A and 604B. Because the real-time images 604A and 604B are consistent with the references images 602A and 602B, the difference images 605A and 605B show very little. Real-time images 606A (top) and 606B (front) are T1-weighted frozen images generated using the techniques disclosed herein. Real-time images 608A (top) and 608B (front) are T2-weighted frozen images generated using the techniques disclosed herein. Real-time images 610A (top) and 610B (front) are PD-weighted frozen images generated using the techniques disclosed herein. FIG. 6B includes reference images 612A (top) and 612B (front). Real-time images 614A (top) and 614B (front) are contrast-variated images generated using the techniques disclosed herein. Images 615A (top) and 615B (front) show the difference between reference images 612A and 612B, and real-time images 614A and 614B. Because the real-time images 614A and 614B are consistent with the references images 612A and 612B, the difference images 615A and 615B show very little. Real-time images 616A (top) and 616B (front) are T1-weighted frozen images generated using the techniques disclosed herein. Real-time images 618A (top) and 618B (front) are T2-weighted frozen images generated using the techniques disclosed herein. Real-time images 620A (top) and 620B (front) are PD-weighted frozen images generated using the techniques disclosed herein. The dotted lines in the front images (lower row) of FIG. 6A and FIG. 6B indicate that the respiratory position in the real-time images obtained using techniques disclosed herein is consistent with the respiratory position in the reference images.

Thus, the real-time images obtained using conventional techniques show consistent motion displacement with the reference images.

In some cases, abrupt motion can present difficulties when obtaining images using the techniques disclosed herein. However, abrupt motion can easily detected by setting an appropriate acceptable range for the principal contrast-transferred temporal weighting function ($\alpha_1$). Any images corresponding to times when $\alpha_1$ exceeds the appropriate acceptable range can be rejected for display.

Aspects of the present disclosure can be used during MR-guided radiation therapy, which generally includes a planning phase with the radiation beam off, and a treatment phase with the radiation beam on. The planning phase can simultaneously serve as the first pulse sequence to learn the spatial factor $U_x$ and the linear transformation T, and the treatment phase can simultaneously be used to generate real-time multi-contrast 3D images with low latency.

While method 200 discusses obtaining the spatial factor $U_x$ and the temporal factor $\Phi$ from the initial k-space data $D_1$, in some implementations the spatial factor $U_x$ and the temporal factor $\Phi$ can be obtained from a set of already-reconstructed images themselves. In some implementations, a set of images of the subject is obtained through any suitable technique. In some examples, the set of images is obtained from the first pulse sequence. In other examples, the set of images is obtained from pulse sequences other than the first pulse sequence. Then, $U_x$ and $\Phi$ can be obtained from these images themselves, instead of directly from the obtained data. The transformation T can then be determined. In these implementations, the transformation T maps the k-space data corresponding to the set of images, to the temporal factor $\Phi$. The second pulse sequence can then be applied to the subject as in method 200 to obtain the real-time k-space data, and the real-time image can be constructed using the spatial factor $U_x$, the temporal factor $\Phi$, and the real-time k-space data obtained with the second pulse sequence. In implementations where the set of images is obtained from the first pulse sequence, the set of images is constructed from the training data $D_1$, and then the spatial factor $U_x$ and the temporal factor $\Phi$ are obtained from the set of images. In implementations where the set of images is obtained from a pulse sequence other than the pulse sequence, the set of images is constructed from data resulting from the pulse sequence, and then the spatial factor $U_x$ and the temporal factor $\Phi$ are obtained from the set of images. Generally, the spatial factor $U_x$ and the temporal factor $\Phi$ can be obtained from any set of images of the subject, so long as the set of images are from the same target location on the subject.

Figure 7:
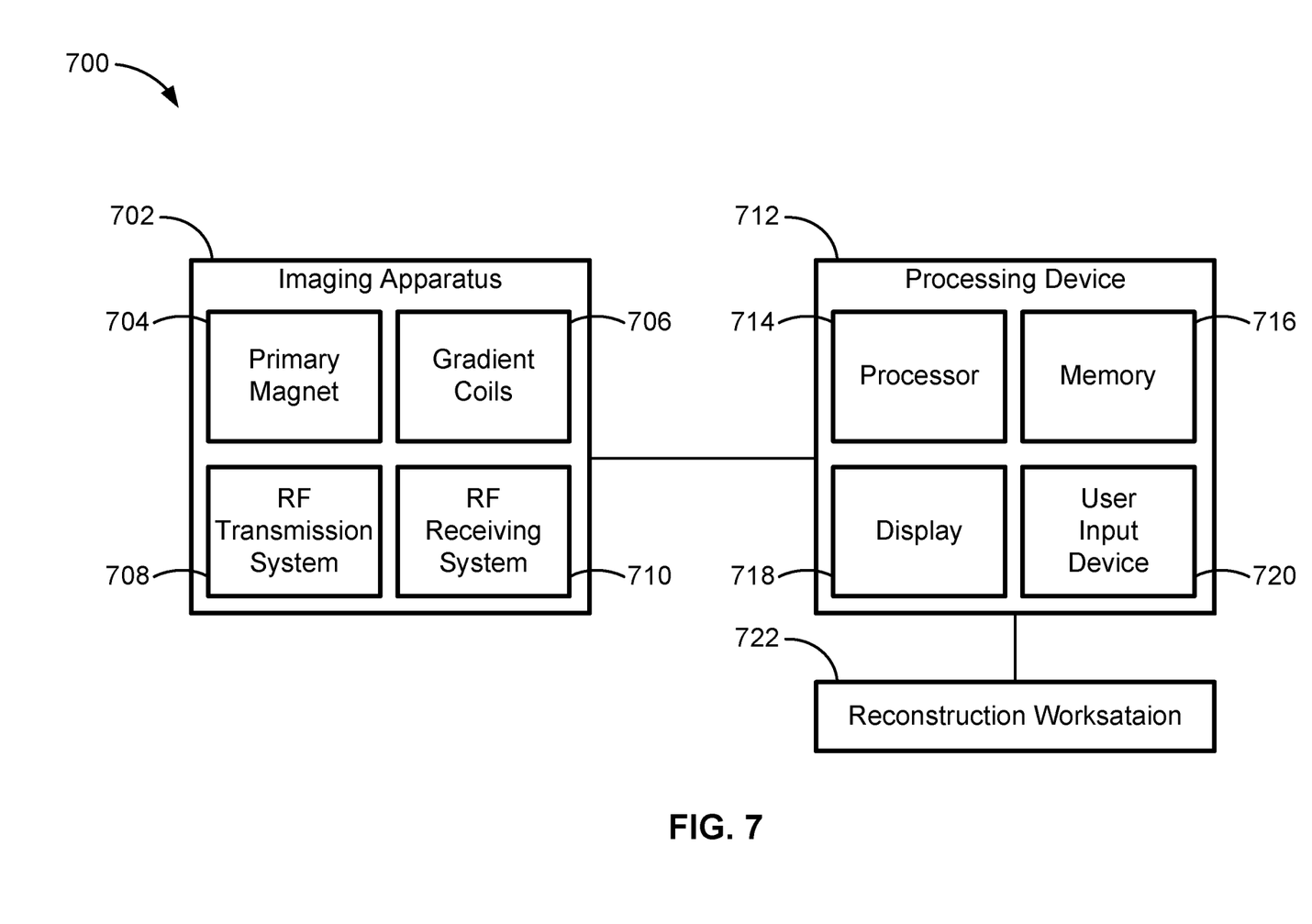
FIG. 7 shows a system for performing magnetic resonance imaging, according to aspects of the present disclosure.

Aspects of the present disclosure can be implemented using a variety of hardware. One such implementation is illustrated in FIG. 7. A system 700 for performing magnetic resonance imaging on a subject includes an imaging apparatus 702, a processing device 712, and a reconstruction workstation 722. The imaging apparatus 702 can be one used for standard magnetic resonance imaging, and can include a primary magnet 704, gradient coils 706, an RF transmission system 708, and an RF receiving system 710. The primary magnet 704 can be a permanent magnet, an electromagnet (such as a coil), or any other suitable magnet. Primary magnet 704 is used to create the external magnet field that is applied to the sample during imaging. Gradient coils 706 create a secondary magnet field that distorts the external magnetic field and can cause the resonant frequency of the protons in the sample to vary by position. The gradient coils 706 can thus be used to spatially encode the positions of protons throughout the sample, e.g. can be used to select which plane intersecting the sample will be used for imaging.

The RF transmission system 708 is used to apply the RF pulse sequence that provides energy to the protons in the sample to rotate their magnet moments out of alignment with the external magnetic field, and saturates the solute material protons. The RF transmission system 708 generally includes a frequency generator (such as an RF synthesizer), a power amplifier, and a transmitting coil. The RF receiving system 710 receives the signals emitted by the protons in the sample as they relax back to their standard alignment. The RF receiving system 710 can a receiving coil to receive the emitted signals, and a pre-amplifier for boosting the received signals and ensuring the signals are suitable for processing. In some implementations, the RF receiving system 710 can include a signal processing component that processes the received signals to provide data that is usable by the processing device 712. Each of the component of the imaging apparatus can be disposed within one or more housings. In some implementations, the imaging apparatus 702 is a 3.0 Tesla clinical scanner equipped with an 18-channel phase array body coil.

The processing device 712 can be communicatively coupled to the imaging apparatus 702, and can include a processor 714, processor-executable memory 716, a display 718, and a user input device 720. The processing device 712 is used to manage the operations of the imaging apparatus 702, and can thus be configured to cause the imaging apparatus 702 to perform dynamic imaging according to the principles disclosed herein. The memory 716 can contain instructions that when executed by processor 714, cause the imaging apparatus 702 to operate as desired. The memory 716 can also store the data obtained from the MRI sequence.

The reconstruction workstation 722 is generally a separate processing device or system that receives the training data and the imaging data from the processing device 712. The reconstruction workstation can be configured as necessary to perform any analysis of the data, include any or all of the steps in method 100 and method 200. In some implementations, the neural network is implemented on the reconstruction workstation 722. In other implementations, the neural network is implemented on separate hardware that can communicate with the reconstruction workstation 722.

In some implementations, a non-transitory, machine-readable medium has instructions stored thereon for implementing any of any of the methods or processes discussed herein. A machine processor is configured to executed the instructions in order to perform these methods or processes.

Aspects of the present disclosure can be implemented on a variety of types of processing devices, such as general purpose computer systems, microprocessors, digital signal processors, micro-controllers, application specific integrated circuits (ASICs), programmable logic devices (PLDs) field programmable logic devices (FPLDs), programmable gate arrays (PGAs), field programmable gate arrays (FPGAs), mobile devices such as mobile telephones, personal digital assistants (PDAs), or tablet computers, local servers, remote servers, wearable computers, or the like.

Memory storage devices of the one or more processing devices can include a machine-readable medium on which is stored one or more sets of instructions (e.g., software) embodying any one or more of the methodologies or functions described herein. The instructions can further be transmitted or received over a network via a network transmitter receiver. While the machine-readable medium can be a single medium, the term "machine-readable medium"

should be taken to include a single medium or multiple media (e.g., a centralized or distributed database, and/or associated caches and servers) that store the one or more sets of instructions. The term "machine-readable medium" can also be taken to include any medium that is capable of storing, encoding, or carrying a set of instructions for execution by the machine and that cause the machine to perform any one or more of the methodologies of the various embodiments, or that is capable of storing, encoding, or carrying data structures utilized by or associated with such a set of instructions. The term "machine-readable medium" can accordingly be taken to include, but not be limited to, solid-state memories, optical media, and magnetic media. A variety of different types of memory storage devices, such as a random access memory (RAM) or a read only memory (ROM) in the system or a floppy disk, hard disk, CD ROM, DVD ROM, flash, or other computer readable medium that is read from and/or written to by a magnetic, optical, or other reading and/or writing system that is coupled to the processing device, can be used for the memory or memories.

While aspects of the present disclosure have been described with reference to one or more particular implementations, those skilled in the art will recognize that many changes may be made thereto without departing from the spirit and scope of the present disclosure. Each of these implementations and obvious variations thereof are contemplated as falling within the spirit and scope of the present disclosure. It is also contemplated that additional implementations according to aspects of the present disclosure may combine any number of features from any of the implementations described herein.

What is claimed is:

1. A method for performing magnetic resonance (MR) imaging on a subject, the method comprising:
   applying a first pulse sequence to a region of interest of the subject using an RF transmission system of an MR imaging apparatus;
   in response to applying the first pulse sequence to the object, obtaining initial k-space data $D_1$ using an RF receiving system of the MR imaging apparatus;
   constructing a spatial factor $U_x$ and a temporal factor $\Phi$ from the initial k-space data $D_1$ using a reconstruction workstation;
   determining a transformation T that maps the initial k-space data $D_1$ to the temporal factor $\Phi$ using the reconstruction workstation;
   applying a second pulse sequence to the object using the RF transmission system;
   obtaining real-time k-space data $D_2$ at time t using the RF receiving system; and
   constructing a real-time image A, where $A=U_x T D_2$, the real-time image A showing the region of interest of the subject at time t using the reconstruction workstation.

2. A system for performing magnetic resonance (MR) imaging on a subject, comprising:
   an MR imaging apparatus that includes:
      a magnet operable to provide a magnetic field;
      an RF transmission system operable to transmit to a region within the magnetic field; and
      an RF receiving system operable to receive a magnetic resonance signal from the region with the magnetic field; and
   a reconstruction workstation,
   wherein the reconstruction workstation is configured to cause the following method to be performed:
      applying a first pulse sequence to a region of interest of the subject using the RF transmission system;
      in response to applying the first pulse sequence to the object, obtaining initial k-space data $D_1$ using the RF receiving system;
      constructing a spatial factor $U_x$ and a temporal factor $\Phi$ from the initial k-space data $D_1$ using the reconstruction workstation;
      determining a transformation T that maps the temporal factor $\Phi$ to the initial k-space data $D_1$ using the reconstruction workstation;
      applying a second pulse sequence to the object using the RF transmission system;
      obtaining real-time k-space data $D_2$ at time t using the RF receiving system;
      constructing a real-time image A, where $A=U_x T D_2$, real-time image A showing the region of interest of the subject at time t using the reconstruction workstation.

3. A non-transitory machine-readable medium having stored thereon instructions for performing magnetic resonance (MR) imaging on a subject, which when executed by at least one processor, cause the following method to be performed:
   applying a first pulse sequence to a region of interest of the subject using an RF transmission system of an MR imaging apparatus;
   in response to applying the first pulse sequence to the object, obtaining initial k-space data $D_1$ using an RF receiving system of the MR imaging apparatus;
   constructing a spatial factor $U_x$ and a temporal factor $\Phi$ from the initial k-space data $D_1$ using a reconstruction workstation;
   determining a transformation T that maps the initial k-space data $D_1$ to the temporal factor $\Phi$ using the reconstruction workstation;
   applying a second pulse sequence to the object using the RF transmission system;
   obtaining real-time k-space data $D_2$ at time t using the RF receiving system; and
   constructing a real-time image A, where $A=U_x T D_2$, real-time image A showing the region of interest of the subject at time t using the reconstruction workstation.

4. A method for performing magnetic resonance (MR) imaging on a subject, the method comprising:
   obtaining a set of images of the subject using a reconstruction workstation;
   constructing a spatial factor $U_x$ and a temporal factor $\Phi$ from the set of images of the subject using the reconstruction workstation;
   determining a transformation T that maps k-space data to the temporal factor $\Phi$, the k-space data corresponding to the set of images using the reconstruction workstation;
   applying a pulse sequence to the object using an RF transmission system of an MR imaging apparatus;
   obtaining real-time k-space data D at time t using an RF receiving system of the MR imaging apparatus; and
   constructing a real-time image A, where $A=U_x T D$, real-time image A showing the region of interest of the subject at time t using the reconstruction workstation.

5. A system for performing magnetic resonance (MR) imaging on a subject, comprising:
   an MR imaging apparatus that includes:
      a magnet operable to provide a magnetic field;
      an RF transmission system operable to transmit to a region within the magnetic field;

an RF receiving system a receiver operable to receive a magnetic resonance signal from the region with the magnetic field; and a reconstruction workstation, wherein the reconstruction workstation is configured to cause the following method to be performed:

obtaining a set of images of the subject using the reconstruction workstation;

constructing a spatial factor $U_x$ and a temporal factor $\Phi$ from the set of images of the subject using the reconstruction workstation;

determining a transformation T that maps k-space data to the temporal factor $\Phi$, the k-space data corresponding to the set of images using the reconstruction workstation;

applying a pulse sequence to the object using the RF transmission system;

obtaining real-time k-space data D at time t using the RF receiving system; and constructing a real-time image A, where $A=U_x TD$, real-time image A showing the region of interest of the subject at time t using the reconstruction workstation.

6. A non-transitory machine-readable medium having stored thereon instructions for performing magnetic resonance (MR) imaging on a subject, which when executed by at least one processor, cause the following method to be performed:

obtaining a set of images of the subject using a reconstruction workstation;

constructing a spatial factor $U_x$ and a temporal factor $\Phi$ from the set of images of the subject using the reconstruction workstation;

determining a transformation T that maps k-space data to the temporal factor $\Phi$, the k-space data corresponding to the set of images using the reconstruction workstation;

applying a pulse sequence to the object using an RF transmission system of an MR imaging apparatus;

obtaining real-time k-space data D at time t using an RF receiving system of an MR imaging apparatus; and constructing a real-time image A, where $A=U_x TD$, real-time image A showing the region of interest of the subject at time t using the reconstruction workstation.

7. The method of claim 1, wherein the initial k-space data $D_1$ includes training data and imaging data.

8. The method of claim 7, wherein the temporal factor $\Phi$ is constructed from the training data.

9. The method of claim 8, wherein the temporal factor $\Phi$ is constructed from only the training data.

10. The method of claim 7, wherein the spatial factor $U_x$ is constructed from the imaging data.

11. The method of claim 10, wherein the spatial factor $U_x$ is constructed from only the imaging data.

12. The method of claim 1, where the real-time k-space data $D_2$ includes only real-time training data, such that the image A is constructed from only real-time training data.

13. The method of claim 1, real-time k-space data $D_2$ is a single k-space line or trajectory.

14. The method of claim 1, wherein the image A is calculated using a fast matrix multiplication procedure.

15. The method of claim 1, wherein T is a linear transformation.

16. The method of claim 1, wherein the image A is obtained with a temporal resolution of about 50 milliseconds.

17. The method of claim 1, wherein the real-time k-space data $D_2$ is obtained within a time period of about 4 milliseconds.

18. The method of claim 17, wherein the image A is constructed from the real-time k-space data $D_2$ within a time period of about 40 milliseconds.

19. The method of claim 17, further comprising:

comparing the initial k-space data $D_1$ and the real-time k-space data $D_2$;

based on the comparison, detecting a bulk motion shift; and updating the spatial factor $U_x$ based at least in part on the detected bulk motion shift.

20. The method of claim 19, wherein the spatial factor $U_x$ is updated prior to constructing the real-time image A.

21. The method of claim 19, wherein the detect bulk motion shift is about 1 millimeter.

22. The method of claim 1, wherein the first pulse sequence and the second pulse sequence form a stack-of-stars acquisition scheme, a Cartesian acquisition scheme, a three-dimensional (3D) radial acquisition scheme, a spiral acquisition scheme, a stack-of-spirals acquisition scheme, an echoplanar acquisition scheme, or any combination thereof.

* * * * *